(12) United States Patent
Van Ess

(10) Patent No.: US 7,101,383 B1
(45) Date of Patent: Sep. 5, 2006

(54) LAPAROSCOPIC INSTRUMENT AND METHOD FOR ITS USE

(76) Inventor: Lester J. Van Ess, Rob-len Farm, 5105 Route 973 East, Cogan Station, PA (US) 17728

( * ) Notice: Subject to any disclaimer, the term of this patent is extended or adjusted under 35 U.S.C. 154(b) by 331 days.

(21) Appl. No.: 10/723,162

(22) Filed: Nov. 26, 2003

(51) Int. Cl.
*A61B 17/28* (2006.01)
(52) U.S. Cl. .................................. 606/207
(58) Field of Classification Search ............... 606/205, 606/211, 107, 190, 159
See application file for complete search history.

(56) References Cited

U.S. PATENT DOCUMENTS

| | | | | |
|---|---|---|---|---|
| 4,452,244 | A | * | 6/1984 | Chin ........................ 606/209 |
| 5,263,967 | A | * | 11/1993 | Lyons et al. ................ 606/205 |
| 5,630,821 | A | * | 5/1997 | Klaas ........................ 606/207 |
| 6,007,554 | A | | 12/1999 | Van Ess |
| 6,595,984 | B1 | | 7/2003 | DeGuillebon |

OTHER PUBLICATIONS

Pages 1-2 from the www.simbionix.com website, Sep. 8, 2003.
Pages 1-4 from the www.spectrumsurgical.com website, Sep. 8, 2003.
14 pages from the www.maheinternational.com website (/lap_cat_2.html) and (/lap_cat_9.html to /lap_cat_14.html), Sep. 8, 2003.

\* cited by examiner

*Primary Examiner*—Kevin T. Truong
(74) *Attorney, Agent, or Firm*—Collard Roe, P.C.

(57) ABSTRACT

A laparoscopic instrument is provided which may be used for propelling a foreign body along an anatomical duct for accessing and removing the foreign body from a patient during surgery. The instrument includes a housing, an elongated body connected to the housing, and an operative tip. The housing includes a first axial bore, a first actuator rod disposed for axial movement within the first axial bore, and an actuator connected to the first actuator rod. The elongated body includes a second axial bore and a second actuator rod connected to the first actuator rod and disposed for axial movement within the second axial bore. The tip includes first and second jaws connected to the elongated body for movement in response to axial movement of the second actuator rod between an open position and a closed position. Each jaw has a respective roller mounted thereon for free rotational movement.

7 Claims, 4 Drawing Sheets

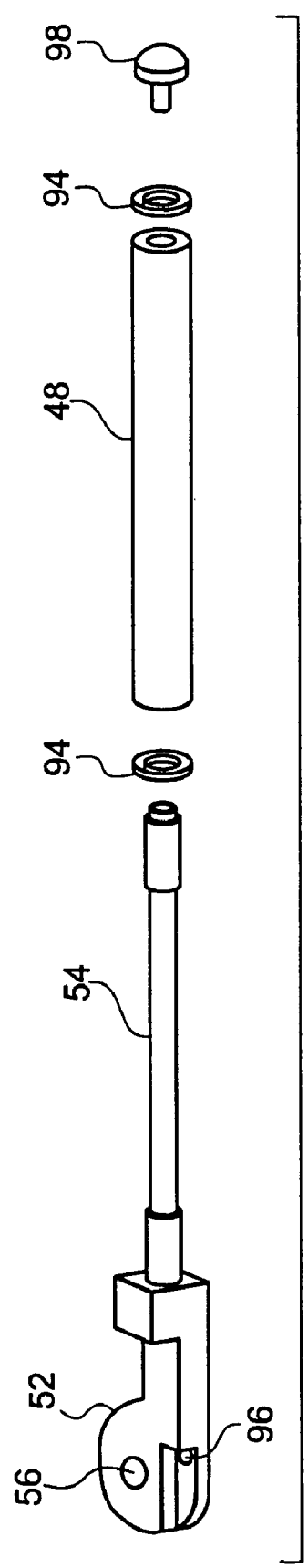

LAPAROSCOPIC INSTRUMENT AND METHOD FOR ITS USE

BACKGROUND OF THE INVENTION

1. Field of the Invention

The present invention relates to a laparoscopic instrument and a method for using same. In particular, the invention relates to a laparoscopic instrument having rotatable rollers in the jaws of the instrument for propelling foreign bodies along anatomical ducts.

2. The Prior Art

Laparoscopic surgical instruments are known which have a manually operable tip, such as cutting blades or forceps, which a surgeon may manipulate from a position external to the abdominal wall of a patient undergoing surgery. See, e.g., U.S. Pat. No. 6,595,984 to DeGuillebon. Although suitable for cutting and retracting operations, these instruments are unsuitable to propel foreign bodies safely along the common duct, the cystic duct, the ureter, or other anatomical duct, in view of the risk of crushing or damaging the lining of the duct from excessive pressure. Hence, there is a need for a laparoscopic instrument and a method that allows a surgeon to safely propel foreign bodies along a duct without the danger of applying excessive pressure so as to damage the duct.

SUMMARY OF THE INVENTION

A laparoscopic instrument and a method for propelling a foreign body along an anatomical duct are provided. In one aspect, the laparoscopic instrument includes a housing, an elongated body connected to the housing, and an operative tip.

The housing includes a first axial bore, a first actuator rod disposed for axial movement within the first axial bore, and an actuator connected to the first actuator rod. The elongated body includes a second axial bore and a second actuator rod connected to the first actuator rod and disposed for axial movement within the second axial bore.

The operative tip includes first and second jaws connected to the elongated body for movement in response to axial movement of the second actuator rod between an open and a closed position. Each jaw has a respective roller mounted thereon for free rotational movement.

In another aspect, the laparoscopic instrument is used in a method for propelling a foreign body along an anatomical duct for accessing and removing the foreign body. In accordance with the method, the laparoscopic instrument is inserted in a closed position into an anatomical cavity. The jaws are opened and then closed in part over an anatomical duct to apply pressure to an interior portion of the duct. The laparoscopic instrument is then moved to cause the rollers to rotate over the anatomical duct to propel the foreign body along the duct to an accessible location for removal.

BRIEF DESCRIPTION OF THE DRAWINGS

Other objects and features of the present invention will become apparent from the following detailed description considered in connection with the accompanying drawings. It should be understood, however, that the drawings are designed for the purpose of illustration only and not as a definition of the limits of the invention.

In the drawings, wherein similar reference characters denote similar elements throughout the several views:

FIG. 4 is an exploded view of one of the jaws and rollers of FIG. 3.

DETAILED DESCRIPTION OF PREFERRED EMBODIMENTS

Figure 1:
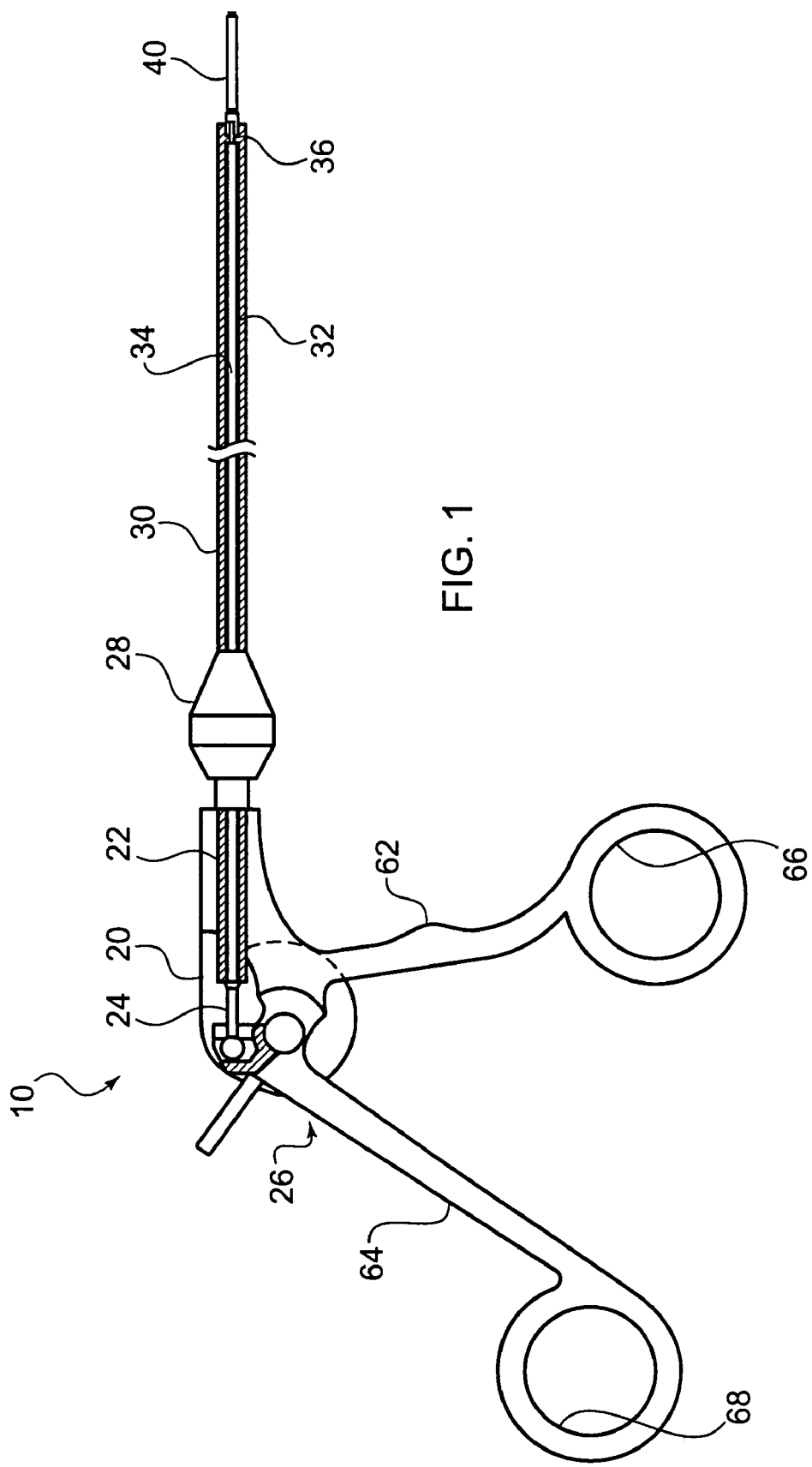
FIG. 1 is an elevation view, partly in section, of a laparoscopic instrument in accordance with one embodiment of the present invention.

Referring now in detail to the drawings and, in particular, FIG. 1, a laparoscopic instrument 10 is shown according to a preferred embodiment of the invention. Instrument 10 includes a housing 20, an elongated body 30 connected to housing 20, and an operative tip 40 operably and preferably removably connected to elongated body 30.

Housing 20 includes, inter alia, a first axial bore 22, a first actuator rod 24 disposed for axial movement within first axial bore 22, and an actuator 26 connected to first actuator rod 24. Actuator 26 includes first and second pivotally connected handles 62, 64. Each handle 62, 64 may have a respective opening 66, 68 for receipt of a user's finger. Preferably, openings 66, 68 are shaped to receive a user's finger or fingers and thumb, respectively, for scissors-like manipulation of the instrument. At least one of the handles, for example handle 62, is connected to first actuator rod 24 and pivotally-movable by the user's finger to cause sliding axial movement of first actuator rod 24 within first axial bore 22. Handle 64 may be stationary or may also be movable by the user's finger.

As shown in FIG. 1, housing 20 may also include a collet closer 28 such as that shown in U.S. Pat. No. 6,595,984 to DeGuillebon including a collet which holds elongated body 30 in conventional manner within housing 20.

Elongated body 30 includes a second axial bore 32 and a second actuator rod 34 operably and removably connected through collet closer 28 at the body end of elongated body 30 to first actuator rod 24 and disposed for axial movement within second axial bore 32 in response to movement of first actuator rod 24 within first axial bore 22 in conventional manner such as is shown in U.S. Pat. No. 6,595,984 to DeGuillebon. Tip end 36 of elongated body 30 is operably connected to tip 40 for actuation of tip 40. Preferably, elongated body 30 has a diameter less than 5 mm so that it may be inserted into a patient through a 5 mm laparoscopic trocar.

Figure 2:
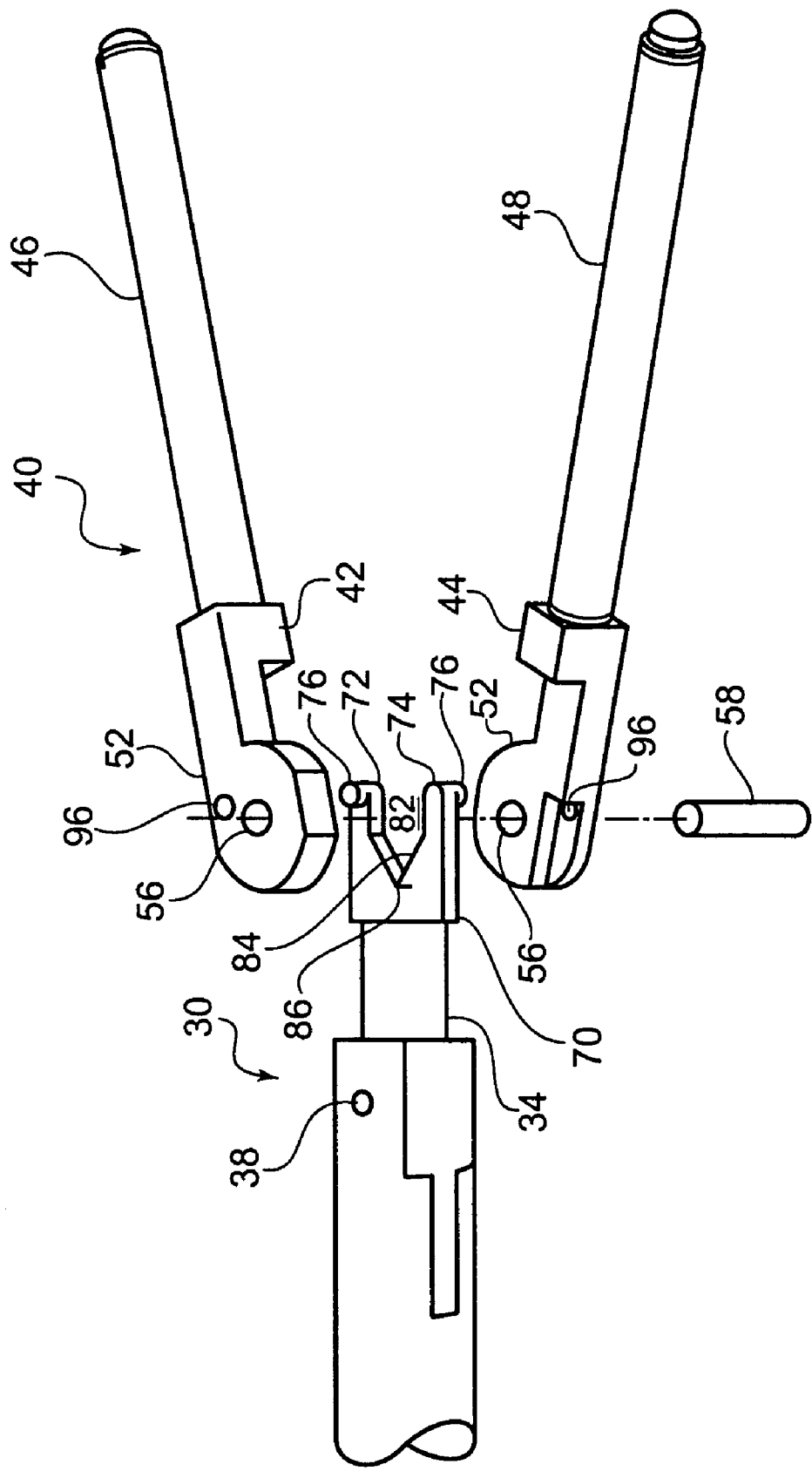
FIG. 2 is an exploded view of the end of the embodiment of FIG. 1 showing the jaws and connection to the elongated body in further detail.
Figure 3:
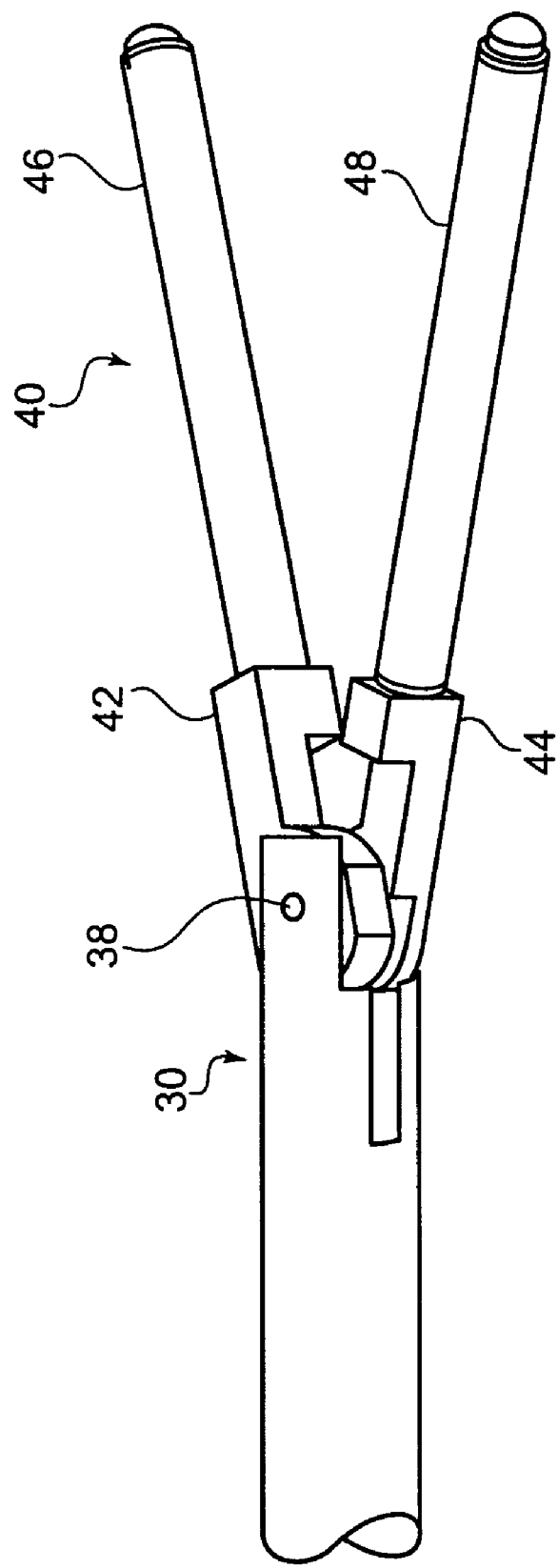
FIG. 3 is an elevation view of the end of the embodiment of FIG. 1 showing the jaws and rollers in an open position.

As shown in FIGS. 2–3, tip 40 includes first and second jaws 42, 44, preferably made of stainless steel, connected to elongated body 30 for movement in response to axial movement by second axial rod 34 between an open position shown in FIG. 3 and a closed position shown in FIG. 1 where jaws 42, 44 are disposed next to each other and aligned generally with elongated body 30 and including positions between the open and closed positions. Each jaw 42, 44 has a respective roller 46, 48, preferably made of stainless steel, mounted thereon for free rotational movement.

As shown in FIG. 4, each jaw 42, 44 includes a pivot portion 52 and a shaft portion 54. Each roller 46, 48 is removably mounted on a shaft portion 54 of jaws 42, 44. Thrust washers 94, preferably made of stainless steel, are disposed on shaft portion 54 on either side of rollers 46, 48. A cap fitting 98 secures the roller on each shaft portion 54 through the distal thrust washer. Each pivot portion 52 has an opening 56 for receipt of a rotatable pin 58 shown in FIG. 2 pivotally mounting jaws 42, 44 to elongated body 30 at pivot opening 38. Rotation of pin 58 causes jaws 42, 44 to move between an open position and a closed position.

As shown in FIG. 2, second actuator rod 34 preferably includes a U-shaped extension 70. Extension 70 includes first and second arms 72, 74 having opposing tubular pegs 76 and a trough 82 having angled edges 84, 86 for rotation of pin 58 in response to axial movement of second actuator rod 34. Each pivot portion 52 includes a peg opening 96 for receipt of a respective peg 76 for rotation of pivot portion 52 about peg 76 in response to axial movement of second actuator rod 34.

In accordance with an embodiment of the method of the invention, laparoscopic instrument 10 is used to propel foreign bodies along an anatomical duct, such as the common duct, the cystic duct, the biliary duct, and ureters, to an area of the duct where foreign bodies are more accessible for removal.

Instrument 10 is first inserted into an anatomical cavity of a patient, preferably via a trocar, such as a 5 mm laparoscopic trocar with jaws 42, 44 in the closed position shown in FIG. 1. Once instrument 10 is inside the patient, the surgeon opens jaws 42, 44 and where necessary closes jaws 42, 44 in part over a duct to apply pressure to an interior portion of the duct, making sure that the pressure exerted is not excessive so as to damage the duct. Jaws 42, 44 are opened and closed by scissor-like movement of handles 62, 64, which effects axial movement of first actuator rod 24 within first axial bore 22. Axial movement of first actuator rod 24 effects axial movement of second actuator rod 34 within and relative to second axial bore 32, which opens and closes jaws 42, 44. Instrument 10 is then moved to cause rollers 46, 48 in the left and right hand jaws 42, 44 of instrument 10 to rotate over the anatomical duct as the foreign body is propelled or "milked" forward along the duct to an accessible location for removal, without the lining of the duct from being crushed or otherwise damaged.

Because zero tolerance exists between jaws 42, 44 in the closed position, at no time will the surgeon fully close jaws 42, 44 over a duct. The only time jaws 42, 44 are positioned in the completely closed position is when the surgeon inserts or removes instrument 10 in or out of the trocar during the laparoscopic surgical procedure. During the surgical procedure, the surgeon, when displaying rollers 46, 48 over a duct will exert, as he or she deems necessary, the required pressure that will safely propel foreign bodies along a duct.

Accordingly, while only a few embodiments of the present invention have been shown and described, it is obvious that many changes and modifications may be made thereunto without departing from the spirit and scope of the invention.

What is claimed is:

1. A laparoscopic instrument comprising:
    (a) a housing including a first axial bore, a first actuator rod disposed for axial movement within the first axial bore, and an actuator connected to said first actuator rod;
    (b) an elongated body having a diameter less than 5 mm connected to said housing comprising a second axial bore and a second actuator rod connected to said first actuator rod and disposed for axial movement within the second axial bore; and
    (c) an operative tip comprising first and second jaws connected to said elongated body for movement between an open position and a closed position in response to axial movement of said second actuator rod, each jaw comprising a pivot portion and a shaft portion and having a respective roller mounted on said jaw for free rotational movement and each roller having a first end and a second end; and
    (d) a respective pair of thrust washers disposed on each shaft portion comprising a proximal thrust washer disposed on the first end of the roller and a distal thrust washer disposed on the second end of the roller and a respective cap fitting securing the roller on the shaft portion through the distal thrust washer;
    wherein said pivot portion has an opening for receipt of a rotatable pin pivotally mounting said first and second jaws, wherein rotation of said pin causes said first and second jaws to move between the open position and the closed position.

2. The laparoscopic instrument according to claim 1 wherein said actuator comprises first and second pivotally connected handles, each handle having an opening for receipt of a user's finger, at least said first handle being connected to said first actuator rod and movable to cause axial movement of said first actuator rod.

3. The laparoscopic instrument according to claim 1 wherein each roller is removably mounted to a corresponding shaft portion.

4. The laparoscopic instrument according to claim 1 wherein said second actuator rod comprises a U-shaped extension including first and second arms having opposing tubular pegs and a trough having angled edges for rotation of said rotatable pin in response to axial movement of said second actuator rod and wherein each pivot portion comprises a peg opening for receipt of a respective peg for rotation of said pivot portion about said peg in response to axial movement of said second actuator rod.

5. A method for propelling a foreign body along an anatomical duct for accessing and removing the foreign body comprising the steps of:
    inserting into an anatomical cavity through a laparoscopic trocar a laparoscopic instrument comprising:
    (a) a housing including a first axial bore, a first actuator rod disposed for axial movement within the first axial bore, and an actuator connected to the first actuator rod;
    (b) an elongated body having a diameter less than 5 mm connected to said housing comprising a second axial bore and a second actuator rod connected to the first actuator rod and disposed for axial movement within the second axial bore; and
    (c) an operative tip comprising first and second jaws connected to said elongated body for movement between an open position and a closed position in response to axial movement of said second actuator rod, each jaw comprising a pivot portion and a shaft portion and having a respective roller mounted on said jaw for free rotational movement and each roller having a first end and a second end; and
    (d) a respective pair of thrust washers disposed on each shaft portion comprising a proximal thrust washer disposed on the first end of the roller and a distal thrust washer disposed on the second end of the roller and a respective cap fitting securing the roller on the shaft portion through the distal thrust washer;
    said laparoscopic instrument being inserted in the closed position;
    opening the jaws;
    closing in part the jaws over an anatomical duct to apply pressure to an interior portion of the duct;

moving the laparoscopic instrument to cause the rollers to rotate over the anatomical duct to propel the foreign body along the duct to an accessible location for removal.

6. The method according to claim 5 wherein said actuator comprises first and second pivotally connected handles, each handle having an opening for receipt of a user's finger, at least said first handle being connected to said first actuator rod and movable to cause axial movement of said first actuator rod and affect opening and closing of the jaws.

7. The method according to claim 5 wherein the anatomical duct is a member of the group consisting of a common duct, a cystic duct, a biliary duct and a ureter.

* * * * *